United States Patent
Dlugos, Jr. et al.

(10) Patent No.: US 8,221,439 B2
(45) Date of Patent: Jul. 17, 2012

(54) POWERING IMPLANTABLE RESTRICTION SYSTEMS USING KINETIC MOTION

(75) Inventors: Daniel F. Dlugos, Jr., Middletown, OH (US); Mark S. Ortiz, Milford, OH (US); Amy L. Marcotte, Mason, OH (US); David N. Plescia, Cincinnati, OH (US); Jason L. Harris, Mason, OH (US); Mark S. Zeiner, Mason, OH (US); Michael J. Stokes, Cincinnati, OH (US); Sean P. Conlon, Loveland, OH (US); David C. Yates, West Chester, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 928 days.

(21) Appl. No.: 12/027,820

(22) Filed: Feb. 7, 2008

(65) Prior Publication Data
US 2009/0204141 A1    Aug. 13, 2009

(51) Int. Cl.
*A61B 17/08* (2006.01)
(52) U.S. Cl. .......................................... 606/151; 600/37
(58) Field of Classification Search ................ 606/151, 606/153; 600/37; 604/8
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzok |
| D23,637 S | 9/1894 | Casad et al. |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |

(Continued)

FOREIGN PATENT DOCUMENTS
CA    1059035    7/1979
(Continued)

OTHER PUBLICATIONS

Eurpoean Search Report mailed Apr. 24, 2009 in EP Application No. 09250304.4.

(Continued)

*Primary Examiner* — Corrine M McDermott
*Assistant Examiner* — Alexander Orkin
(74) *Attorney, Agent, or Firm* — Nutter McClennen & Fish LLP

(57) ABSTRACT

Various powering devices are provided for transferring and/or generating energy from numerous sources to a communicating member implanted in a patient. The energy transferred to or generated by the communicating member can be used to provide power to an implantable restriction system configured to form a restriction in a pathway.

12 Claims, 5 Drawing Sheets

U.S. PATENT DOCUMENTS

| | | |
|---|---|---|
| 899,477 A | 9/1908 | Williams |
| 926,197 A | 6/1909 | Kim |
| 953,875 A | 4/1910 | Waring |
| 991,192 A | 5/1911 | Battenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | McK. Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Riekse |
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |

| | | | | | | |
|---|---|---|---|---|---|---|
| 3,238,624 A | 3/1966 | McCabe | | 3,512,517 A | 5/1970 | Kadish et al. |
| 3,240,510 A | 3/1966 | Spouge | | 3,514,919 A | 6/1970 | Ashton et al. |
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,487 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison et al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper et al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley et al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine et al. |
| 3,463,338 A | 8/1969 | Schneider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,616 A | 4/1973 | Lenzkes |
| 3,472,230 A | 10/1969 | Fogarty | | 3,730,174 A | 5/1973 | Madison |
| 3,478,344 A | 11/1969 | Schwitzgebel et al. | | 3,730,560 A | 5/1973 | Abildgaard et al. |
| 3,482,449 A | 12/1969 | Werner | | 3,731,679 A | 5/1973 | Wilhelmson et al. |
| 3,482,816 A | 12/1969 | Arnold | | 3,731,681 A | 5/1973 | Blackshear et al. |
| 3,487,959 A | 1/1970 | Pearne et al. | | 3,732,731 A | 5/1973 | Fussell, Jr. |
| 3,491,842 A | 1/1970 | Delacour et al. | | 3,735,040 A | 5/1973 | Punt et al. |
| 3,492,638 A | 1/1970 | Lane | | 3,736,930 A | 6/1973 | Georgi |
| 3,502,829 A | 3/1970 | Reynolds | | 3,738,356 A | 6/1973 | Workman |
| 3,503,116 A | 3/1970 | Strack | | 3,740,921 A | 6/1973 | Meyer et al. |
| 3,504,664 A | 4/1970 | Haddad | | 3,746,111 A | 7/1973 | Berthiaume et al. |
| 3,505,808 A | 4/1970 | Eschle | | 3,748,678 A | 7/1973 | Ballou |
| 3,509,754 A | 5/1970 | Massingill et al. | | 3,749,098 A | 7/1973 | De Bennetot et al. |

| | | | | | | |
|---|---|---|---|---|---|---|
| 3,749,422 A | 7/1973 | Abildgaard et al. | | 3,923,060 A | 12/1975 | Ellinwood, Jr. |
| 3,749,423 A | 7/1973 | Abildgaard et al. | | 3,924,635 A | 12/1975 | Hakim et al. |
| 3,750,194 A | 8/1973 | Summers | | 3,928,980 A | 12/1975 | Ganzinotti et al. |
| 3,757,770 A | 9/1973 | Brayshaw et al. | | 3,929,175 A | 12/1975 | Coone |
| 3,759,095 A | 9/1973 | Short, Jr. et al. | | 3,930,682 A | 1/1976 | Booth |
| 3,760,638 A | 9/1973 | Lawson et al. | | 3,930,852 A | 1/1976 | Tanaka et al. |
| 3,763,960 A | 10/1973 | John et al. | | 3,936,028 A | 2/1976 | Norton et al. |
| 3,765,142 A | 10/1973 | Lindquist et al. | | 3,940,122 A | 2/1976 | Janzen et al. |
| 3,765,494 A | 10/1973 | Kielman, Jr. | | 3,940,630 A | 2/1976 | Bergonz |
| 3,769,156 A | 10/1973 | Brecy et al. | | 3,942,299 A | 3/1976 | Bory et al. |
| 3,769,830 A | 11/1973 | Porter et al. | | 3,942,382 A | 3/1976 | Hok et al. |
| 3,774,243 A | 11/1973 | Ng et al. | | 3,942,516 A | 3/1976 | Glynn et al. |
| 3,776,333 A | 12/1973 | Mathauser | | 3,942,536 A | 3/1976 | Mirowski et al. |
| 3,778,051 A | 12/1973 | Allen et al. | | 3,943,915 A | 3/1976 | Severson |
| 3,780,578 A | 12/1973 | Sellman et al. | | 3,945,704 A | 3/1976 | Kraus et al. |
| 3,781,902 A | 12/1973 | Shim et al. | | 3,946,613 A | 3/1976 | Silver |
| 3,783,585 A | 1/1974 | Hoyland et al. | | 3,946,615 A | 3/1976 | Hluchan |
| 3,789,667 A | 2/1974 | Porter et al. | | 3,946,724 A | 3/1976 | La Balme et al. |
| 3,796,095 A | 3/1974 | Fussell, Jr. | | 3,948,141 A | 4/1976 | Shinjo et al. |
| 3,807,219 A | 4/1974 | Wallskog | | 3,949,388 A | 4/1976 | Fuller |
| 3,811,429 A | 5/1974 | Fletcher et al. | | 3,953,289 A | 4/1976 | Costes et al. |
| 3,815,722 A | 6/1974 | Sessoms | | 3,954,271 A | 5/1976 | Tredway, Sr. |
| 3,818,765 A | 6/1974 | Eriksen et al. | | 3,958,558 A | 5/1976 | Dunphy et al. |
| 3,820,400 A | 6/1974 | Russo | | 3,961,425 A | 6/1976 | Swanson et al. |
| 3,820,795 A | 6/1974 | Taylor | | 3,961,646 A | 6/1976 | Schon et al. |
| 3,823,610 A | 7/1974 | Fussell, Jr. | | 3,962,895 A | 6/1976 | Rydell et al. |
| 3,825,065 A | 7/1974 | Lloyd et al. | | 3,962,921 A | 6/1976 | Lips |
| 3,825,963 A | 7/1974 | Abildgaard et al. | | 3,963,019 A | 6/1976 | Quandt |
| 3,825,964 A | 7/1974 | Groswith, III et al. | | 3,964,485 A | 6/1976 | Neumeier |
| 3,828,672 A | 8/1974 | Gazzola et al. | | 3,964,770 A | 6/1976 | Abildgaard et al. |
| 3,828,766 A | 8/1974 | Krasnow | | 3,967,737 A | 7/1976 | Peralta et al. |
| 3,831,588 A | 8/1974 | Rindner | | 3,968,473 A | 7/1976 | Patton et al. |
| 3,831,942 A | 8/1974 | Del Mar | | 3,968,694 A | 7/1976 | Clark |
| 3,833,238 A | 9/1974 | Liard et al. | | 3,972,320 A | 8/1976 | Kalman |
| 3,834,167 A | 9/1974 | Tabor | | 3,973,753 A | 8/1976 | Wheeler |
| 3,834,739 A | 9/1974 | Abildgaard et al. | | 3,973,858 A | 8/1976 | Poisson et al. |
| 3,835,523 A | 9/1974 | Stansfield et al. | | 3,974,655 A | 8/1976 | Halpern et al. |
| 3,839,708 A | 10/1974 | Bredesen et al. | | 3,974,865 A | 8/1976 | Fenton et al. |
| 3,842,483 A | 10/1974 | Cramer | | 3,977,391 A | 8/1976 | Fleischmann |
| 3,842,668 A | 10/1974 | Lippke et al. | | 3,980,871 A | 9/1976 | Lindstrom et al. |
| 3,845,664 A | 11/1974 | Perry, Jr. | | 3,982,571 A | 9/1976 | Fenton et al. |
| 3,845,751 A | 11/1974 | Runstetler | | 3,983,948 A | 10/1976 | Jeter |
| 3,845,757 A | 11/1974 | Weyer | | 3,985,133 A | 10/1976 | Jenkins et al. |
| 3,847,434 A | 11/1974 | Weman et al. | | 3,987,860 A | 10/1976 | Jabsen |
| 3,850,208 A | 11/1974 | Hamilton | | 3,989,005 A | 11/1976 | Bowler, Jr. et al. |
| 3,853,117 A | 12/1974 | Murr | | 3,991,749 A | 11/1976 | Zent |
| 3,854,469 A | 12/1974 | Giori et al. | | 3,992,948 A | 11/1976 | D'Antonio et al. |
| 3,855,902 A | 12/1974 | Kirst et al. | | 3,993,149 A | 11/1976 | Harvey |
| 3,857,399 A | 12/1974 | Zacouto et al. | | 3,996,927 A | 12/1976 | Frank |
| 3,857,452 A | 12/1974 | Hartman | | 3,996,962 A | 12/1976 | Sutherland |
| 3,857,745 A | 12/1974 | Grausch et al. | | 4,003,141 A | 1/1977 | Le Roy |
| 3,858,581 A | 1/1975 | Kamen | | 4,005,282 A | 1/1977 | Jennings |
| 3,863,622 A | 2/1975 | Buuck | | 4,005,593 A | 2/1977 | Goldberg |
| 3,863,933 A | 2/1975 | Tredway | | 4,006,735 A | 2/1977 | Hittman et al. |
| 3,867,950 A | 2/1975 | Fischell | | 4,009,375 A | 2/1977 | White et al. |
| 3,868,008 A | 2/1975 | Brumbaugh | | 4,009,591 A | 3/1977 | Hester |
| 3,868,679 A | 2/1975 | Arneson | | 4,010,449 A | 3/1977 | Faggin et al. |
| 3,871,599 A | 3/1975 | Takada et al. | | 4,014,319 A | 3/1977 | Favre et al. |
| 3,872,285 A | 3/1975 | Shum et al. | | 4,014,321 A | 3/1977 | March |
| 3,874,388 A | 4/1975 | King et al. | | 4,016,764 A | 4/1977 | Rice |
| 3,876,980 A | 4/1975 | Haemmig et al. | | 4,017,329 A | 4/1977 | Larson |
| 3,878,908 A | 4/1975 | Andersson et al. | | 4,018,134 A | 4/1977 | Linsinger et al. |
| 3,881,528 A | 5/1975 | Mackenzie | | 4,022,190 A | 5/1977 | Meyer |
| 3,893,111 A | 7/1975 | Cotter | | 4,024,864 A | 5/1977 | Davies et al. |
| 3,893,451 A | 7/1975 | Durand et al. | | 4,025,912 A | 5/1977 | Rice |
| 3,895,681 A | 7/1975 | Griffin et al. | | 4,026,276 A | 5/1977 | Chubbuck |
| 3,899,862 A | 8/1975 | Muys et al. | | 4,027,661 A | 6/1977 | Lyon et al. |
| 3,904,234 A | 9/1975 | Hill et al. | | 4,031,899 A | 6/1977 | Renirie et al. |
| 3,908,334 A | 9/1975 | Rychiger et al. | | 4,036,775 A | 7/1977 | Trautvetter et al. |
| 3,908,461 A | 9/1975 | Turpen | | 4,039,069 A | 8/1977 | Kwan et al. |
| 3,908,721 A | 9/1975 | McGahey et al. | | 4,041,954 A | 8/1977 | Ohara et al. |
| 3,910,087 A | 10/1975 | Jones | | 4,042,504 A | 8/1977 | Drori et al. |
| 3,912,168 A | 10/1975 | Mullins et al. | | 4,045,345 A | 8/1977 | Drori et al. |
| 3,912,304 A | 10/1975 | Abildgaard et al. | | 4,047,851 A | 9/1977 | Bender |
| 3,918,286 A | 11/1975 | Whitehead | | 4,048,494 A | 9/1977 | Liesting et al. |
| 3,918,291 A | 11/1975 | Pauly et al. | | 4,048,879 A | 9/1977 | Cox |
| 3,920,965 A | 11/1975 | Sohrwardy et al. | | 4,049,004 A | 9/1977 | Walters |
| 3,921,682 A | 11/1975 | McGahey et al. | | 4,051,338 A | 9/1977 | Harris, III |
| 3,922,951 A | 12/1975 | Linsinger et al. | | 4,052,991 A | 10/1977 | Zacouto et al. |

| | | |
|---|---|---|
| 4,055,074 A | 10/1977 | Thimons et al. |
| 4,055,175 A | 10/1977 | Clemens et al. |
| 4,056,854 A | 11/1977 | Boretos et al. |
| 4,058,007 A | 11/1977 | Exner et al. |
| 4,062,351 A | 12/1977 | Hastwell et al. |
| 4,062,354 A | 12/1977 | Taylor et al. |
| 4,062,360 A | 12/1977 | Bentley |
| 4,063,439 A | 12/1977 | Besson et al. |
| 4,064,882 A | 12/1977 | Johnson et al. |
| 4,070,239 A | 1/1978 | Bevilacqua |
| 4,072,047 A | 2/1978 | Reismuller et al. |
| 4,073,292 A | 2/1978 | Edelman |
| 4,075,099 A | 2/1978 | Pelton et al. |
| 4,075,602 A | 2/1978 | Clothier |
| 4,077,072 A | 3/1978 | Dezura et al. |
| 4,077,394 A | 3/1978 | McCurdy |
| 4,077,405 A | 3/1978 | Haerten et al. |
| 4,077,882 A | 3/1978 | Gangemi |
| 4,078,620 A | 3/1978 | Westlake et al. |
| 4,080,653 A | 3/1978 | Barnes, Jr. et al. |
| 4,084,752 A | 4/1978 | Hagiwara et al. |
| 4,086,488 A | 4/1978 | Hill |
| 4,087,568 A | 5/1978 | Fay et al. |
| 4,088,417 A | 5/1978 | Kosmowski |
| 4,089,329 A | 5/1978 | Couvillon, Jr. et al. |
| 4,090,802 A | 5/1978 | Bilz et al. |
| 4,092,719 A | 5/1978 | Salmon et al. |
| 4,092,925 A | 6/1978 | Fromson |
| 4,096,866 A | 6/1978 | Fischell |
| 4,098,293 A | 7/1978 | Kramer et al. |
| 4,103,496 A | 8/1978 | Colamussi et al. |
| 4,106,370 A | 8/1978 | Kraus et al. |
| 4,107,689 A | 8/1978 | Jellinek |
| 4,107,995 A | 8/1978 | Ligman et al. |
| 4,108,148 A | 8/1978 | Cannon, III |
| 4,108,575 A | 8/1978 | Schal |
| 4,109,148 A | 8/1978 | Jaulmes et al. |
| 4,109,518 A | 8/1978 | Dooley et al. |
| 4,109,644 A | 8/1978 | Kojima |
| 4,111,056 A | 9/1978 | Mastromatteo |
| 4,111,629 A | 9/1978 | Nussbaumer et al. |
| 4,114,424 A | 9/1978 | Johnson |
| 4,114,606 A | 9/1978 | Seylar |
| 4,120,097 A | 10/1978 | Jeter |
| 4,120,134 A | 10/1978 | Scholle |
| 4,121,635 A | 10/1978 | Hansel |
| 4,123,310 A | 10/1978 | Varon et al. |
| 4,124,023 A | 11/1978 | Fleischmann et al. |
| 4,127,110 A | 11/1978 | Bullara |
| 4,130,169 A | 12/1978 | Denison |
| 4,131,596 A | 12/1978 | Allen |
| 4,133,355 A | 1/1979 | Mayer |
| 4,133,367 A | 1/1979 | Abell |
| 4,140,131 A | 2/1979 | Dutcher et al. |
| 4,141,348 A | 2/1979 | Hittman |
| 4,141,349 A | 2/1979 | Ory et al. |
| 4,143,661 A | 3/1979 | LaForge et al. |
| 4,146,029 A | 3/1979 | Ellinwood, Jr. |
| 4,147,161 A | 4/1979 | Ikebe et al. |
| 4,148,096 A | 4/1979 | Haas et al. |
| 4,149,423 A | 4/1979 | Frosch et al. |
| 4,151,823 A | 5/1979 | Grosse et al. |
| 4,153,085 A | 5/1979 | Adams |
| 4,156,422 A | 5/1979 | Hildebrandt et al. |
| 4,160,448 A | 7/1979 | Jackson |
| 4,160,971 A | 7/1979 | Jones et al. |
| 4,166,469 A | 9/1979 | Littleford |
| 4,167,304 A | 9/1979 | Gelbke |
| 4,167,952 A | 9/1979 | Reinicke |
| 4,168,567 A | 9/1979 | Leguy et al. |
| 4,170,280 A | 10/1979 | Schwarz |
| 4,171,218 A | 10/1979 | Hoshino et al. |
| 4,183,124 A | 1/1980 | Hoffman |
| 4,183,247 A | 1/1980 | Allen et al. |
| 4,185,641 A | 1/1980 | Minior et al. |
| 4,186,287 A | 1/1980 | Scott |
| 4,186,749 A | 2/1980 | Fryer |
| 4,186,751 A | 2/1980 | Fleischmann |
| 4,190,057 A | 2/1980 | Hill et al. |
| 4,191,004 A | 3/1980 | Gmuer et al. |
| 4,191,187 A | 3/1980 | Wright et al. |
| 4,192,192 A | 3/1980 | Schnell |
| 4,193,397 A | 3/1980 | Tucker et al. |
| 4,204,547 A | 5/1980 | Allocca |
| 4,206,755 A | 6/1980 | Klein et al. |
| 4,206,761 A | 6/1980 | Cosman |
| 4,206,762 A | 6/1980 | Cosman |
| 4,207,903 A | 6/1980 | O'Neill |
| 4,212,074 A | 7/1980 | Kuno et al. |
| 4,217,221 A | 8/1980 | Masso |
| 4,217,588 A | 8/1980 | Freeny, Jr. |
| 4,220,189 A | 9/1980 | Marquez |
| 4,221,219 A | 9/1980 | Tucker |
| 4,221,523 A | 9/1980 | Eberle |
| 4,223,837 A | 9/1980 | Gubbiotti et al. |
| 4,226,124 A | 10/1980 | Kersten et al. |
| 4,226,229 A | 10/1980 | Eckhart et al. |
| 4,227,533 A | 10/1980 | Godfrey |
| 4,231,376 A | 11/1980 | Lyon et al. |
| 4,232,682 A | 11/1980 | Veth |
| 4,237,900 A | 12/1980 | Schulman et al. |
| 4,241,247 A | 12/1980 | Byrne et al. |
| 4,241,870 A | 12/1980 | Marcus |
| 4,245,593 A | 1/1981 | Stein |
| 4,246,877 A | 1/1981 | Kennedy |
| 4,247,850 A | 1/1981 | Marcus |
| 4,248,238 A | 2/1981 | Joseph et al. |
| 4,248,241 A | 2/1981 | Tacchi |
| 4,256,094 A | 3/1981 | Kapp et al. |
| 4,256,118 A | 3/1981 | Nagel et al. |
| 4,262,343 A | 4/1981 | Claycomb |
| 4,262,632 A | 4/1981 | Hanton et al. |
| 4,265,241 A | 5/1981 | Portner et al. |
| 4,265,252 A | 5/1981 | Chubbuck et al. |
| 4,271,018 A | 6/1981 | Drori et al. |
| 4,273,070 A | 6/1981 | Hoefelmayr et al. |
| 4,274,444 A | 6/1981 | Ruyak |
| 4,275,600 A | 6/1981 | Turner et al. |
| 4,275,913 A | 6/1981 | Marcus |
| 4,278,540 A | 7/1981 | Drori et al. |
| 4,280,036 A | 7/1981 | Fukatsu et al. |
| 4,280,775 A | 7/1981 | Wood |
| 4,281,666 A | 8/1981 | Cosman |
| 4,281,667 A | 8/1981 | Cosman |
| 4,284,073 A | 8/1981 | Krause et al. |
| 4,285,770 A | 8/1981 | Chi et al. |
| 4,291,699 A | 9/1981 | Geddes et al. |
| 4,295,963 A | 10/1981 | Drori et al. |
| 4,297,927 A | 11/1981 | Kuroda et al. |
| 4,303,075 A | 12/1981 | Heilman et al. |
| 4,305,402 A | 12/1981 | Katims |
| 4,312,374 A | 1/1982 | Drori et al. |
| 4,314,480 A | 2/1982 | Becker |
| 4,316,693 A | 2/1982 | Baxter et al. |
| 4,325,387 A | 4/1982 | Helfer |
| 4,327,804 A | 5/1982 | Reed |
| 4,328,654 A | 5/1982 | Van Ginkel et al. |
| 4,332,254 A | 6/1982 | Lundquist |
| 4,339,831 A | 7/1982 | Johnson |
| 4,342,218 A | 8/1982 | Fox |
| 4,342,308 A | 8/1982 | Trick |
| 4,346,604 A | 8/1982 | Snook et al. |
| 4,347,851 A | 9/1982 | Jundanian |
| 4,350,647 A | 9/1982 | de la Cruz |
| 4,350,970 A | 9/1982 | von Tomkewitsch et al. |
| 4,351,037 A | 9/1982 | Scherbatskoy |
| 4,351,116 A | 9/1982 | Scott, Jr. |
| 4,356,486 A | 10/1982 | Mount |
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Shimazoe et al. |
| 4,365,425 A | 12/1982 | Gotchel |
| 4,368,937 A | 1/1983 | Palombo et al. |
| 4,369,013 A | 1/1983 | Abildgaard et al. |
| 4,373,527 A | 2/1983 | Fischell |
| 4,376,523 A | 3/1983 | Goyen et al. |

| | | | | | | |
|---|---|---|---|---|---|---|
| 4,378,809 A | 4/1983 | Cosman | | 4,503,678 A | 3/1985 | Wimbush et al. |
| 4,380,427 A | 4/1983 | Hehl et al. | | 4,511,974 A | 4/1985 | Nakane et al. |
| 4,385,636 A | 5/1983 | Cosman | | 4,513,295 A | 4/1985 | Jones et al. |
| 4,386,422 A | 5/1983 | Mumby et al. | | 4,515,004 A | 5/1985 | Jaenson |
| 4,387,907 A | 6/1983 | Hiestand et al. | | 4,515,750 A | 5/1985 | Pardini et al. |
| 4,392,368 A | 7/1983 | Folkesson et al. | | 4,516,866 A | 5/1985 | Yamauchi et al. |
| 4,393,899 A | 7/1983 | Tsuji et al. | | 4,518,637 A | 5/1985 | Takeda et al. |
| 4,393,951 A | 7/1983 | Horst-Rudolf et al. | | 4,519,401 A | 5/1985 | Ko et al. |
| 4,395,232 A | 7/1983 | Koch | | 4,520,443 A | 5/1985 | Yuki et al. |
| 4,395,258 A | 7/1983 | Wang et al. | | 4,522,213 A | 6/1985 | Wallroth et al. |
| 4,395,916 A | 8/1983 | Martin | | 4,527,568 A | 7/1985 | Rickards et al. |
| 4,398,983 A | 8/1983 | Suzuki et al. | | 4,529,401 A | 7/1985 | Leslie et al. |
| 4,399,705 A | 8/1983 | Weiger et al. | | 4,531,526 A | 7/1985 | Genest |
| 4,399,707 A | 8/1983 | Wamstad | | 4,531,936 A | 7/1985 | Gordon |
| 4,399,809 A | 8/1983 | Baro et al. | | 4,536,000 A | 8/1985 | Rohm et al. |
| 4,399,821 A | 8/1983 | Bowers | | 4,537,005 A | 8/1985 | Hoyland et al. |
| 4,403,984 A | 9/1983 | Ash et al. | | 4,537,129 A | 8/1985 | Heinemann et al. |
| 4,404,968 A | 9/1983 | Evans, Sr. | | 4,538,616 A | 9/1985 | Rogoff |
| 4,404,974 A | 9/1983 | Titus | | 4,540,404 A | 9/1985 | Wolvek |
| 4,405,318 A | 9/1983 | Whitney et al. | | 4,542,461 A | 9/1985 | Eldridge et al. |
| 4,407,125 A | 10/1983 | Parsons et al. | | 4,544,369 A | 10/1985 | Skakoon et al. |
| 4,407,271 A | 10/1983 | Schiff | | 4,545,185 A | 10/1985 | Chikatani et al. |
| 4,407,296 A | 10/1983 | Anderson | | 4,546,524 A | 10/1985 | Kreft |
| 4,407,326 A | 10/1983 | Wilhelm | | 4,548,209 A | 10/1985 | Wielders et al. |
| 4,408,597 A | 10/1983 | Tenney, Jr. | | 4,552,150 A | 11/1985 | Zacouto et al. |
| 4,408,615 A | 10/1983 | Grossman | | 4,553,226 A | 11/1985 | Scherbatskoy |
| 4,415,071 A | 11/1983 | Butler et al. | | 4,556,063 A | 12/1985 | Thompson et al. |
| 4,416,282 A | 11/1983 | Saulson et al. | | 4,557,269 A | 12/1985 | Reynolds et al. |
| 4,418,899 A | 12/1983 | Zimmermann et al. | | 4,557,332 A | 12/1985 | Denison et al. |
| 4,419,393 A | 12/1983 | Hanson et al. | | 4,559,815 A | 12/1985 | Needham et al. |
| 4,421,505 A | 12/1983 | Schwartz | | 4,560,979 A | 12/1985 | Rosskopf et al. |
| 4,424,720 A | 1/1984 | Bucchianeri | | 4,561,442 A | 12/1985 | Vollmann et al. |
| 4,428,228 A | 1/1984 | Banzhaf et al. | | 4,562,751 A | 1/1986 | Nason et al. |
| 4,428,365 A | 1/1984 | Hakky et al. | | 4,563,175 A | 1/1986 | LaFond |
| 4,430,899 A | 2/1984 | Wessel et al. | | 4,565,116 A | 1/1986 | Hehl et al. |
| 4,431,009 A | 2/1984 | Marino, Jr. et al. | | 4,566,456 A | 1/1986 | Koning et al. |
| 4,431,365 A | 2/1984 | Sturtz, Jr. | | 4,569,623 A | 2/1986 | Goldmann |
| 4,432,363 A | 2/1984 | Kakegawa et al. | | 4,570,351 A | 2/1986 | Szanto et al. |
| 4,435,173 A | 3/1984 | Siposs et al. | | 4,571,161 A | 2/1986 | Leblanc et al. |
| 4,439,186 A | 3/1984 | Kuhl et al. | | 4,571,995 A | 2/1986 | Timme |
| 4,441,491 A | 4/1984 | Evans, Sr. | | 4,573,835 A | 3/1986 | Eckardt et al. |
| 4,441,501 A | 4/1984 | Parent | | 4,574,792 A | 3/1986 | Trick |
| 4,444,194 A | 4/1984 | Burcham | | 4,576,181 A | 3/1986 | Wallace et al. |
| 4,444,498 A | 4/1984 | Heinemann | | 4,576,183 A | 3/1986 | Plicchi et al. |
| 4,445,385 A | 5/1984 | Endo | | 4,577,512 A | 3/1986 | Lowenheck et al. |
| 4,446,711 A | 5/1984 | Valente | | 4,581,018 A | 4/1986 | Jassawalla et al. |
| 4,447,224 A | 5/1984 | DeCant, Jr. et al. | | 4,581,915 A | 4/1986 | Haulsee et al. |
| 4,449,493 A | 5/1984 | Kopec et al. | | 4,587,840 A | 5/1986 | Dobler et al. |
| 4,450,811 A | 5/1984 | Ichikawa et al. | | 4,589,805 A | 5/1986 | Duffner et al. |
| 4,451,033 A | 5/1984 | Nestegard | | 4,592,339 A | 6/1986 | Kuzmak et al. |
| 4,453,537 A | 6/1984 | Spitzer | | 4,592,340 A | 6/1986 | Boyles |
| 4,453,578 A | 6/1984 | Wilder | | 4,593,703 A | 6/1986 | Cosman |
| 4,460,835 A | 7/1984 | Masuoka et al. | | 4,595,228 A | 6/1986 | Chu |
| 4,464,170 A | 8/1984 | Clemens et al. | | 4,596,563 A | 6/1986 | Pande |
| 4,465,015 A | 8/1984 | Osta et al. | | 4,599,943 A | 7/1986 | Kobler et al. |
| 4,465,474 A | 8/1984 | Mardorf et al. | | 4,600,855 A | 7/1986 | Strachan et al. |
| 4,466,290 A | 8/1984 | Frick | | 4,602,541 A | 7/1986 | Benzinger et al. |
| 4,468,172 A | 8/1984 | Dixon et al. | | 4,604,089 A | 8/1986 | Santangelo et al. |
| 4,468,762 A | 8/1984 | Jurgens et al. | | 4,605,354 A | 8/1986 | Daly |
| 4,469,365 A | 9/1984 | Marcus et al. | | 4,606,419 A | 8/1986 | Perini |
| 4,471,182 A | 9/1984 | Wielgos et al. | | 4,606,478 A | 8/1986 | Hack et al. |
| 4,471,786 A | 9/1984 | Inagaki et al. | | 4,610,256 A | 9/1986 | Wallace |
| 4,473,067 A | 9/1984 | Schiff | | 4,614,137 A | 9/1986 | Jones |
| 4,473,078 A | 9/1984 | Angel | | 4,617,016 A | 10/1986 | Blomberg et al. |
| 4,476,721 A | 10/1984 | Hochreuther et al. | | 4,618,861 A | 10/1986 | Gettens et al. |
| 4,478,213 A | 10/1984 | Redding | | 4,620,807 A | 11/1986 | Polit |
| 4,478,538 A | 10/1984 | Kakino et al. | | 4,621,331 A | 11/1986 | Iwata et al. |
| 4,483,196 A | 11/1984 | Kurtz et al. | | 4,622,871 A | 11/1986 | Van Sickle et al. |
| 4,484,135 A | 11/1984 | Ishihara et al. | | 4,626,462 A | 12/1986 | Kober et al. |
| 4,485,813 A | 12/1984 | Anderson et al. | | 4,633,304 A | 12/1986 | Nagasaki et al. |
| 4,489,916 A | 12/1984 | Stevens | | 4,633,878 A | 1/1987 | Bombardieri et al. |
| 4,492,632 A | 1/1985 | Mattson | | 4,635,182 A | 1/1987 | Hintz |
| 4,494,411 A | 1/1985 | Koschke et al. | | 4,637,736 A | 1/1987 | Andeen et al. |
| 4,494,950 A | 1/1985 | Fischell | | 4,638,665 A | 1/1987 | Benson et al. |
| 4,497,176 A | 2/1985 | Rubin et al. | | 4,644,246 A | 2/1987 | Knapen et al. |
| 4,497,201 A | 2/1985 | Allen et al. | | 4,646,553 A | 3/1987 | Tufte et al. |
| 4,499,394 A | 2/1985 | Koal | | 4,648,363 A | 3/1987 | Kronich |
| 4,499,691 A | 2/1985 | Karazim et al. | | 4,648,406 A | 3/1987 | Miller |
| 4,499,750 A | 2/1985 | Gerber et al. | | 4,658,358 A | 4/1987 | Leach et al. |

| | | |
|---|---|---|
| 4,658,760 A | 4/1987 | Zebuhr |
| 4,660,568 A | 4/1987 | Cosman |
| 4,665,511 A | 5/1987 | Rodney et al. |
| 4,665,896 A | 5/1987 | LaForge et al. |
| 4,669,484 A | 6/1987 | Masters |
| 4,672,974 A | 6/1987 | Lee |
| 4,674,457 A | 6/1987 | Berger et al. |
| 4,674,546 A | 6/1987 | Fournier et al. |
| 4,678,408 A | 7/1987 | Nason et al. |
| 4,681,559 A | 7/1987 | Hooven |
| 4,683,850 A | 8/1987 | Bauder et al. |
| 4,685,463 A | 8/1987 | Williams |
| 4,685,469 A | 8/1987 | Keller et al. |
| 4,685,903 A | 8/1987 | Cable et al. |
| 4,686,987 A | 8/1987 | Salo et al. |
| 4,687,530 A | 8/1987 | Berscheid et al. |
| 4,689,979 A | 9/1987 | Otsuka et al. |
| 4,691,694 A | 9/1987 | Boyd et al. |
| 4,691,710 A | 9/1987 | Dickens et al. |
| 4,693,253 A | 9/1987 | Adams |
| 4,695,237 A | 9/1987 | Inaba et al. |
| 4,696,189 A | 9/1987 | Hochreuther et al. |
| 4,697,574 A | 10/1987 | Karcher et al. |
| 4,698,038 A | 10/1987 | Key et al. |
| 4,700,497 A | 10/1987 | Sato et al. |
| 4,700,610 A | 10/1987 | Bauer et al. |
| 4,701,143 A | 10/1987 | Key et al. |
| 4,703,756 A | 11/1987 | Gough et al. |
| 4,705,507 A | 11/1987 | Boyles |
| 4,706,948 A | 11/1987 | Kroecher et al. |
| 4,712,562 A | 12/1987 | Ohayon et al. |
| 4,718,425 A | 1/1988 | Tanaka et al. |
| 4,722,348 A | 2/1988 | Ligtenberg et al. |
| 4,724,806 A | 2/1988 | Hartwig et al. |
| 4,724,830 A | 2/1988 | Fischell |
| 4,725,826 A | 2/1988 | Hunter |
| 4,728,479 A | 3/1988 | Merkovsky |
| 4,729,517 A | 3/1988 | Krokor et al. |
| 4,730,188 A | 3/1988 | Milheiser |
| 4,730,420 A | 3/1988 | Stratmann et al. |
| 4,730,619 A | 3/1988 | Koning et al. |
| 4,731,058 A | 3/1988 | Doan |
| 4,735,205 A | 4/1988 | Chachques et al. |
| 4,738,267 A | 4/1988 | Lazorthes et al. |
| 4,738,268 A | 4/1988 | Kipnis |
| 4,741,345 A | 5/1988 | Matthews et al. |
| 4,741,732 A | 5/1988 | Crankshaw et al. |
| 4,743,129 A | 5/1988 | Keryhuel et al. |
| 4,745,541 A | 5/1988 | Vaniglia et al. |
| 4,746,830 A | 5/1988 | Holland |
| 4,750,495 A | 6/1988 | Moore et al. |
| 4,752,115 A | 6/1988 | Murray, Jr. et al. |
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,798,227 A | 1/1989 | Goodwin |
| 4,799,491 A | 1/1989 | Eckerle |
| 4,799,625 A | 1/1989 | Weaver, Jr. et al. |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |
| 4,840,350 A | 6/1989 | Cook et al. |
| 4,844,002 A | 7/1989 | Yasui et al. |
| 4,846,153 A | 7/1989 | Berci |
| 4,846,191 A | 7/1989 | Brockway et al. |
| 4,846,664 A | 7/1989 | Hehl et al. |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach et al. |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold et al. |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio et al. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |
| 4,932,406 A | 6/1990 | Berkovits |
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |

| | | |
|---|---|---|
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |
| 5,298,022 A | 3/1994 | Bernardi et al. |
| 5,298,884 A | 3/1994 | Gilmore et al. |

| | | | | | | |
|---|---|---|---|---|---|---|
| 5,300,093 A | 4/1994 | Koestner et al. | | 5,509,888 A | 4/1996 | Miller |
| 5,300,120 A | 4/1994 | Knapp et al. | | 5,509,891 A | 4/1996 | DeRidder |
| 5,304,112 A | 4/1994 | Mrklas et al. | | 5,513,945 A | 5/1996 | Hartmann et al. |
| 5,305,923 A | 4/1994 | Kirschner et al. | | 5,514,103 A | 5/1996 | Srisathapat et al. |
| 5,312,443 A | 5/1994 | Adams et al. | | 5,518,504 A | 5/1996 | Polyak |
| 5,312,452 A | 5/1994 | Salo | | 5,520,606 A | 5/1996 | Schoolman et al. |
| 5,312,453 A | 5/1994 | Shelton et al. | | 5,523,740 A | 6/1996 | Burgmann et al. |
| 5,313,953 A | 5/1994 | Yomtov et al. | | 5,534,018 A | 7/1996 | Wahlstrand et al. |
| 5,314,451 A | 5/1994 | Mulier | | 5,535,752 A | 7/1996 | Halperin et al. |
| 5,314,457 A | 5/1994 | Jeutter et al. | | 5,538,005 A | 7/1996 | Harrison et al. |
| 5,324,315 A | 6/1994 | Grevious | | 5,541,857 A | 7/1996 | Walter et al. |
| 5,325,834 A | 7/1994 | Ballheimer et al. | | 5,545,140 A | 8/1996 | Conero et al. |
| 5,326,249 A | 7/1994 | Weissfloch et al. | | 5,545,151 A | 8/1996 | O'Connor et al. |
| 5,328,460 A | 7/1994 | Lord et al. | | 5,545,186 A | 8/1996 | Olson et al. |
| 5,330,511 A | 7/1994 | Boute et al. | | 5,545,214 A | 8/1996 | Stevens |
| 5,337,750 A | 8/1994 | Walloch | | 5,547,470 A | 8/1996 | Johnson et al. |
| 5,341,430 A | 8/1994 | Aulia et al. | | 5,551,427 A | 9/1996 | Altman |
| 5,342,401 A | 8/1994 | Spano et al. | | 5,551,439 A | 9/1996 | Hickey |
| 5,342,406 A | 8/1994 | Thompson | | 5,554,185 A | 9/1996 | Block et al. |
| 5,344,388 A | 9/1994 | Maxwell et al. | | 5,558,644 A | 9/1996 | Boyd et al. |
| 5,347,476 A | 9/1994 | McBean, Sr. | | 5,564,434 A | 10/1996 | Halperin et al. |
| 5,348,210 A | 9/1994 | Linzell et al. | | 5,575,770 A | 11/1996 | Melsky et al. |
| 5,348,536 A | 9/1994 | Young et al. | | 5,584,803 A | 12/1996 | Stevens et al. |
| 5,350,413 A | 9/1994 | Miller et al. | | 5,586,629 A | 12/1996 | Shoberg et al. |
| 5,352,180 A | 10/1994 | Candelon et al. | | 5,593,430 A | 1/1997 | Renger |
| 5,353,622 A | 10/1994 | Theener | | 5,594,665 A | 1/1997 | Walter et al. |
| 5,353,800 A | 10/1994 | Pohndorf et al. | | 5,596,986 A | 1/1997 | Goldfarb |
| 5,354,200 A | 10/1994 | Klein et al. | | 5,597,284 A | 1/1997 | Weltlich et al. |
| 5,354,316 A | 10/1994 | Keimel | | 5,610,083 A | 3/1997 | Chan et al. |
| 5,354,319 A | 10/1994 | Wyborny et al. | | 5,611,768 A | 3/1997 | Tutrone, Jr. |
| 5,360,407 A | 11/1994 | Leonard et al. | | 5,612,497 A | 3/1997 | Walter et al. |
| 5,365,462 A | 11/1994 | McBean, Sr. | | 5,615,671 A | 4/1997 | Schoonen et al. |
| 5,365,619 A | 11/1994 | Solomon | | 5,619,991 A | 4/1997 | Sloane |
| 5,365,985 A | 11/1994 | Todd et al. | | 5,625,946 A | 5/1997 | Wildeson et al. |
| 5,368,040 A | 11/1994 | Carney | | 5,626,623 A | 5/1997 | Kieval et al. |
| 5,370,665 A | 12/1994 | Hudrlik | | 5,626,630 A | 5/1997 | Markowitz et al. |
| 5,373,852 A | 12/1994 | Harrison et al. | | 5,630,836 A | 5/1997 | Prem et al. |
| 5,375,073 A | 12/1994 | McBean | | 5,634,255 A | 6/1997 | Bishop et al. |
| 5,377,128 A | 12/1994 | McBean | | 5,637,083 A | 6/1997 | Bertrand et al. |
| 5,378,231 A | 1/1995 | Johnson et al. | | 5,643,207 A | 7/1997 | Rise |
| 5,382,232 A | 1/1995 | Hague et al. | | 5,645,116 A | 7/1997 | McDonald |
| 5,383,915 A | 1/1995 | Adams | | 5,650,766 A | 7/1997 | Burgmann et al. |
| 5,388,578 A | 2/1995 | Yomtov et al. | | 5,673,585 A | 10/1997 | Bishop et al. |
| 5,388,586 A | 2/1995 | Lee et al. | | 5,676,690 A | 10/1997 | Noren et al. |
| 5,388,831 A | 2/1995 | Quadri et al. | | 5,681,285 A | 10/1997 | Ford et al. |
| 5,394,909 A | 3/1995 | Mitchell et al. | | 5,686,831 A | 11/1997 | Vandervalk et al. |
| 5,402,944 A | 4/1995 | Pape et al. | | 5,687,734 A | 11/1997 | Dempsey et al. |
| 5,406,957 A | 4/1995 | Tansey | | 5,693,076 A | 12/1997 | Kaemmerer |
| 5,409,009 A | 4/1995 | Olson | | 5,702,368 A | 12/1997 | Stevens et al. |
| 5,411,031 A | 5/1995 | Yomtov | | 5,702,427 A | 12/1997 | Ecker et al. |
| 5,411,551 A | 5/1995 | Winston et al. | | 5,702,431 A | 12/1997 | Wang et al. |
| 5,411,552 A | 5/1995 | Andersen et al. | | 5,704,352 A | 1/1998 | Tremblay et al. |
| 5,416,372 A | 5/1995 | Ljungstroem et al. | | 5,715,786 A | 2/1998 | Seiberth et al. |
| 5,417,226 A | 5/1995 | Juma | | 5,715,837 A | 2/1998 | Chen |
| 5,417,717 A | 5/1995 | Salo et al. | | 5,720,436 A | 2/1998 | Buschor et al. |
| 5,425,362 A | 6/1995 | Siker et al. | | 5,730,101 A | 3/1998 | Aupperle et al. |
| 5,431,171 A | 7/1995 | Harrison et al. | | 5,732,710 A | 3/1998 | Rabinovich et al. |
| 5,431,694 A | 7/1995 | Snaper et al. | | 5,733,313 A | 3/1998 | Barreras, Sr. et al. |
| 5,433,694 A | 7/1995 | Lim et al. | | 5,738,652 A | 4/1998 | Boyd et al. |
| 5,437,605 A | 8/1995 | Helmy et al. | | 5,742,233 A | 4/1998 | Hoffman et al. |
| 5,443,215 A | 8/1995 | Fackler | | 5,743,267 A | 4/1998 | Nikolic et al. |
| 5,447,519 A | 9/1995 | Peterson | | 5,749,369 A | 5/1998 | Rabinovich et al. |
| 5,449,368 A | 9/1995 | Kuzmak | | 5,749,909 A | 5/1998 | Schroeppel et al. |
| 5,456,690 A | 10/1995 | Duong-Van | | 5,755,687 A | 5/1998 | Donlon |
| 5,461,390 A | 10/1995 | Hoshen | | 5,755,748 A | 5/1998 | Borza et al. |
| 5,464,435 A | 11/1995 | Neumann | | 5,765,568 A | 6/1998 | Sweezer, Jr. et al. |
| 5,467,627 A | 11/1995 | Smith et al. | | 5,769,812 A | 6/1998 | Stevens et al. |
| 5,474,226 A | 12/1995 | Joseph | | 5,771,903 A | 6/1998 | Jakobsson |
| 5,479,818 A | 1/1996 | Walter et al. | | 5,782,774 A | 7/1998 | Shmulewitz |
| 5,482,049 A | 1/1996 | Addiss et al. | | 5,787,520 A | 8/1998 | Dunbar |
| 5,487,760 A | 1/1996 | Villafana | | 5,791,344 A | 8/1998 | Schulman et al. |
| 5,493,738 A | 2/1996 | Sanderson et al. | | 5,792,094 A | 8/1998 | Stevens et al. |
| 5,494,036 A | 2/1996 | Uber, III et al. | | 5,792,179 A | 8/1998 | Sideris |
| 5,494,193 A | 2/1996 | Kirschner et al. | | 5,795,325 A | 8/1998 | Valley et al. |
| 5,504,474 A | 4/1996 | Libman et al. | | 5,796,827 A | 8/1998 | Coppersmith et al. |
| 5,505,916 A | 4/1996 | Berry, Jr. | | 5,800,375 A | 9/1998 | Sweezer et al. |
| 5,507,412 A | 4/1996 | Ebert et al. | | 5,807,265 A | 9/1998 | Itoigawa et al. |
| 5,507,737 A | 4/1996 | Palmskog et al. | | 5,807,336 A | 9/1998 | Russo et al. |
| 5,507,785 A | 4/1996 | Deno | | 5,810,015 A | 9/1998 | Flaherty |

| | | | |
|---|---|---|---|
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,871,526 A | 2/1999 | Gibbs |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,916,179 A | 6/1999 | Sharrock |
| 5,916,237 A | 6/1999 | Schu |
| 5,935,078 A | 8/1999 | Feierbach |
| 5,938,669 A | 8/1999 | Klaiber et al. |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,030,413 A | 2/2000 | Lazarus |
| 6,035,461 A | 3/2000 | Nguyen |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A | 5/2000 | Forsell et al. |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,131,664 A | 10/2000 | Sonnier |
| 6,135,945 A | 10/2000 | Sultan |
| 6,159,156 A | 12/2000 | Van Bockel et al. |
| 6,162,180 A | 12/2000 | Miesel et al. |
| 6,162,245 A | 12/2000 | Jayaraman et al. |
| 6,168,614 B1 | 1/2001 | Andersen et al. |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,482,145 B1 | 11/2002 | Forsell et al. |
| 6,482,171 B1 | 11/2002 | Corvi et al. |
| 6,482,177 B1 | 11/2002 | Leinders et al. |
| 6,485,462 B1 | 11/2002 | Kriesel |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | VanTassel et al. |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |

| | | |
|---|---|---|
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 7,844,342 B2 | 11/2010 | Dlugos et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0021322 A1 | 2/2004 | Ariav |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0102026 A1 | 5/2005 | Turner et al. |
| 2005/0143765 A1* | 6/2005 | Bachmann et al. ............ 606/157 |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0256549 A1 | 11/2005 | Holzer |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0247737 A1 | 11/2006 | Olson et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |
| 2008/0249806 A1 | 10/2008 | Dlugos et al. |
| 2008/0250341 A1 | 10/2008 | Dlugos et al. |
| 2009/0204179 A1 | 8/2009 | Dlugos et al. |
| 2009/0222065 A1 | 9/2009 | Dlugos et al. |

FOREIGN PATENT DOCUMENTS

| | | |
|---|---|---|
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| EP | 1832254 A1 | 9/2007 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0033738 | 6/2000 |
| WO | WO-0072899 | 12/2000 |
| WO | WO-0104487 | 1/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006113187 | 10/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

Eurpoean Search Report mailed Jun. 9, 2009 in EP Application No. 09250306.9.

European Search Report, Application No. EP09250301, issued Jun. 4, 2009, 2 pages.

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page, Sep. 2008.

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page, Sep. 2008.

"Radiation Hardened Electronics and Radiation Technology", Honeywell product and service information from website http://www.honeywell.com/sites/portal?smap=aerospace&page=Radiation-Hardened-Electronics&theme=T4; 2 pages, Sep. 2008.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

European Examination Report issued Feb. 16, 2011 for Application No. 09250304.4 (4 pages).

* cited by examiner

POWERING IMPLANTABLE RESTRICTION SYSTEMS USING KINETIC MOTION

FIELD OF THE INVENTION

The present invention relates to methods and devices for providing power to implantable restriction systems.

BACKGROUND OF THE INVENTION

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. Traditionally, adjusting a gastric band required a scheduled clinician visit during which a Huber needle and syringe were used to penetrate the patient's skin and add or remove fluid from the balloon via the injection port. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits command signals to the implant. The implant in turn adjusts the band and transmits a response command to the programmer.

Implants such as those described above include electronics which require a power source that is sufficient for the intended function, such as making adjustments to the gastric band. Such devices may be internally powered by a battery or capacitor while others may be powered by an externally coupled power source or passive telemetry system. When coupling externally, the efficiencies between the implant and external device diminish substantially as the distance between them increases. There can also be significant power losses through tissue.

Accordingly, there is a need for methods and devices for charging implanted electronics efficiently through tissue by using external and/or non-invasive techniques. It would also be advantageous for a patient to be able to recharge implants without having to travel to a scheduled clinician visit.

SUMMARY OF THE INVENTION

The present invention provides methods and devices for providing power to an implantable restriction system. In one exemplary embodiment, a system for forming a restriction in a patient is provided and includes an implantable restriction device adapted to form a restriction in a pathway within a patient. For example, the implantable restriction device can include a gastric band and a housing in communication with the gastric band. The implantable restriction device can also include a communicating member that powers the implantable restriction device. The system can further include an external apparatus that is operable to communicate with the communicating member by sending power and/or data signals to the communicating member and/or by receiving data signals from the communicating member. The communicating member can also be configured to send data signals to an external device. The external apparatus can optionally include a gauge that is effective to indicate whether the external apparatus is effectively communicating with the communicating member.

In one embodiment, the communicating member can be adapted to convert light waves into energy, and the external apparatus can be an energy transfer apparatus having a light source that is operable to communicate light to the communicating member. The energy transfer apparatus can include a gauge effective to indicate whether the light waves are being communicated between the light source and the communicating member effective to power the implantable restriction device or communicate data. In an embodiment, the communicating member can be a photovoltaic cell array, a silicon nanowire bundle, or a crystalline silicon cell array, and the light source can emit infrared light waves in a range of about 0.70 .mu.m to 1,000 .mu.m. Alternatively, the light source can emit visible light waves in a range of about 400 nm to 1,000 nm or ultraviolet light waves in a range of about 280 nm to 400 nm.

In another embodiment, the communicating member can be adapted to utilize a temperature differential to power the implantable restriction device, the energy transfer apparatus can have a temperature source operable to create a temperature differential across the communicating member to power the implantable restriction device. In an exemplary embodiment, the communicating member is a thermogenerator. The temperature source can be, for example, ice, a thermoelectric cooler, a heating source, and a blood vessel. The communicating member can be configured to utilize a temperature differential between the temperature source and an anatomical reference temperature to produce energy to power the implantable restriction device. In another embodiment, the gauge can be effective to indicate whether a temperature differential exists between the temperature source and the communicating member effective to power the implantable restriction device.

In another embodiment, the communicating member can have a kinetic motion apparatus operable to convert motion into energy to power the implantable restriction device. The kinetic motion apparatus can include a housing, a magnet disposed within the housing, and a wire coil disposed around the housing. The wire coil can be in electrical communication with the implantable restriction device and the magnet can be configured to move relative to the wire coil to create electrical energy to power the implantable restriction device. The kinetic motion apparatus can further include a storage device for storing the electrical energy produced from movement of the magnet. The system may also include an external device that may include a driver adapted to produce corresponding oscillations, vibrations, or other motions in the kinetic motion apparatus effective to power the implantable restriction device. Alternatively, an external oscillating electromagnet can induce sympathetic oscillations in the magnet disposed within the housing. In another embodiment, the gauge can be adapted to indicate a charge status of the implantable restriction device.

In a further exemplary embodiment, a kinetic motion apparatus can include a counterweight coupled to a drive gear and configured to rotate freely about a pivot point when the kinetic motion apparatus is rotated in response to patient movement. The kinetic motion apparatus can also include an electric generator configured to receive mechanical energy from the drive gear and convert it to electrical energy to power the implantable restriction device.

In one embodiment, a kinetic motion apparatus can include a piezoelectric device configured to convert internal muscle and/or organ movement within a patient into electrical energy to power the implantable restriction device. The piezoelectric device can also be configured to convert digestive movement of a patient's stomach against the gastric band into electrical energy to power the implantable restriction device.

Methods are also provided for powering an implantable restriction device. In one embodiment, the method can include activating a light source to transfer light through tissue to a communicating member disposed within an implantable restriction device. The communicating member can convert the light to electrical current to power the implantable restriction device. The light source can be on an external device, and the method can further include positioning the external device adjacent to a skin surface and in proximity to the communicating member implanted within tissue. The external device can also optionally include a gauge that indicates whether light transferred between the light source and the communicating member is effective to power the implantable restriction device. Additionally, the external device can receive data from the communicating member which includes at least one measurement of pressure of fluid within the implantable restriction device. In an exemplary embodiment, the light source emits infrared light with a wavelength in a range of about 0.70 μm to 1,000 μm. Alternatively, the light source emits visible light with a wavelength in a range of about 400 nm to 750 nm or ultraviolet light with a wavelength in the range of about 280 nm to 400 nm.

In another embodiment, a method is provided for powering an implantable restriction device and includes placing a temperature source on a tissue surface adjacent to a communicating member disposed within an implantable restriction device implanted in a patient. The communicating member utilizes a temperature differential to power the implantable restriction device. The communicating member may be placed close to the skin such that it resides in a temperature gradient between the external environment and the body core. Alternatively, the thermogenerator can be placed in contact with a large blood vessel since the body uses the blood stream to convey heat to and from the body. Thus, a natural temperature gradient exists in the body with may be used to generate power. The temperature source can be on an external device, and the external device can receive data from the communicating member. The external device can also include a gauge that indicates whether a temperature differential exists between the temperature source and the communicating member effective to power the implantable restriction device. The data can include at least one measurement of pressure of fluid within the implantable restriction device. In one embodiment, the temperature source can be ice, a thermoelectric cooler, and/or a heating source placed on or near a tissue surface adjacent to the thermogenerator creating a temperature differential with an anatomical reference temperature across the thermogenerator to produce electrical current to power the implantable restriction device.

In still another embodiment, a method for providing power to an implantable restriction device is provided and includes driving a communicating member coupled to an implantable restriction device implanted in a patient to power the implantable restriction device, where the communicating member includes a kinetic motion apparatus. The kinetic motion apparatus can include a metal wire and a magnet and the metal wire and a magnetic field created by the magnet move relative to one another, thereby generating electrical energy to power the implantable restriction device. In an exemplary embodiment, the metal wire and the magnetic field move relative to one another in response to motion by the patient. The kinetic motion apparatus can also be driven by an external oscillating electromagnet that induces sympathetic oscillations in the magnet. Alternatively, the kinetic motion apparatus is driven by a vibration element that causes the metal wire to move through the magnetic field. In another embodiment, the communicating member can be in communication with an external device that receives data from the communicating member and which can include a gauge that indicates a charge status of the implantable restriction device. The kinetic motion apparatus can alternatively include a counterweight coupled to a drive gear that rotates freely about a pivot point in response to patient movement. Rotation of the counterweight and drive gear can generate mechanical energy that is converted into electrical energy to power the implantable restriction device. In one exemplary embodiment, the kinetic motion apparatus includes a piezoelectric device that converts internal muscle and/or organ movement within a patient into energy to power the implantable restriction device. The piezoelectric device can also convert digestive motion of the stomach against the gastric band into electrical energy to power the implantable restriction device. The method can include storing excess energy generated by the kinetic motion apparatus in a storage device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
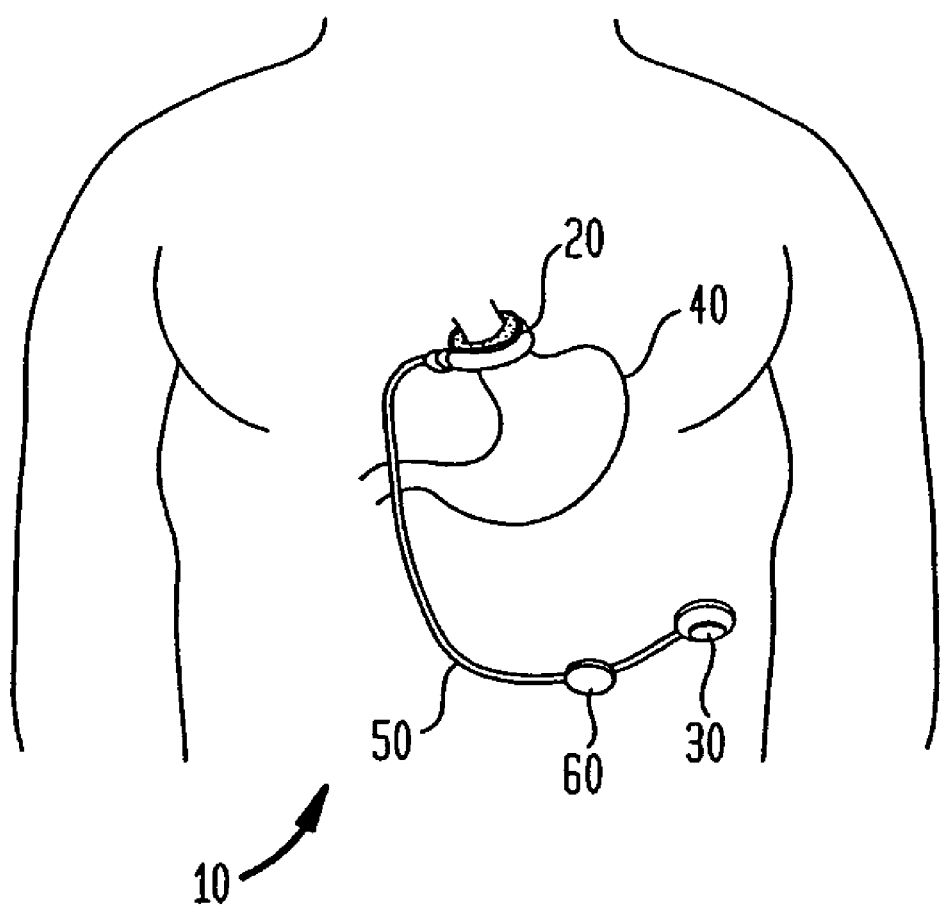
FIG. 1 is a representation of a food intake restriction system implanted in a patient to form a restriction in the patient's stomach.

Various powering devices are provided for transferring energy from an external source through tissue to a communicating member implanted in a patient. The energy transferred to the communicating member can be used to provide power to an implantable restriction device that is implanted to form a restriction in a pathway within a patient. While the present invention disclosed herein can be used with a variety of implantable restriction devices known in the art, FIG. 1 illustrates one exemplary embodiment of a food intake restriction system 10. As shown, the system 10 generally includes an adjustable gastric band 20 that is configured to be positioned around the upper portion of a patient's stomach 40. In addition, the system 10 can include a communicating member capable of providing power to various devices configured to perform any number of tasks within the system 10, as will be described below.

The communicating member can be located anywhere in the system 10. For example, in one embodiment, the communicating member can be disposed within an injection port 30 shown in FIG. 1. The injection port 30 can be in fluid communication with the gastric band for allowing fluid to be introduced into and removed from the band to alter the amount of restriction provided by the band. Alternatively, or in addition, the communicating member can be disposed within a housing 60 that can house various components. In the illustrated embodiment, the system 10 includes both an injection port 30 and a housing 60. Both the injection port 30 and the housing 60 are coupled to the adjustable gastric band 20, e.g., via a catheter 50. A person skilled in the art will appreciate that the system need not include an injection port and/or housing, and that the communicating member can be positioned anywhere along the system 10.

In an exemplary embodiment, the communicating member can convert energy received from an external source to provide power to devices within the system 10 that measure and/or monitor various conditions of the system 10, that make adjustments to the gastric band 20 and/or other aspects of the system 10, and/or that measure/monitor various physiological parameters. Such devices can include, for example, sensors, pumps, bands and/or any other monitoring and/or adjustment devices having circuitry which requires electrical power. The communicating member can be configured to repeatedly receive energy from an external source, convert the energy to electrical power, and store the power in a capacitor, battery or other power storage device known in the art for later use by the device(s) within the system 10. Alternatively, the communicating member can be configured to transfer the converted power directly to the device(s) as needed. In addition, the communicating member can be configured to transmit and receive data to and from an external source. For example, the communicating member can receive command signals from an external source related to powering the system 10. The communicating member can also transmit various anatomical measurements taken within a patient's body to an external device or reader, as well as to transmit information regarding the charge status of the system 10.

The communicating member can take any form known in the art, and various embodiments of the communicating member are provided in detail below. In certain exemplary embodiments, the communicating member can take the form of a sensor capable of receiving energy from an external source for measuring and monitoring various parameters of the system 10; an antenna such as a dipole antenna, a monopole antenna with appropriate counterpoise, or an inductive coil capable of receiving energy through tissue; and/or any other devices known in the art which are capable of aiding in the powering, measuring, monitoring, and/or adjusting of the system 10 and/or other physiological parameters associated with the system 10.

Figure 2:
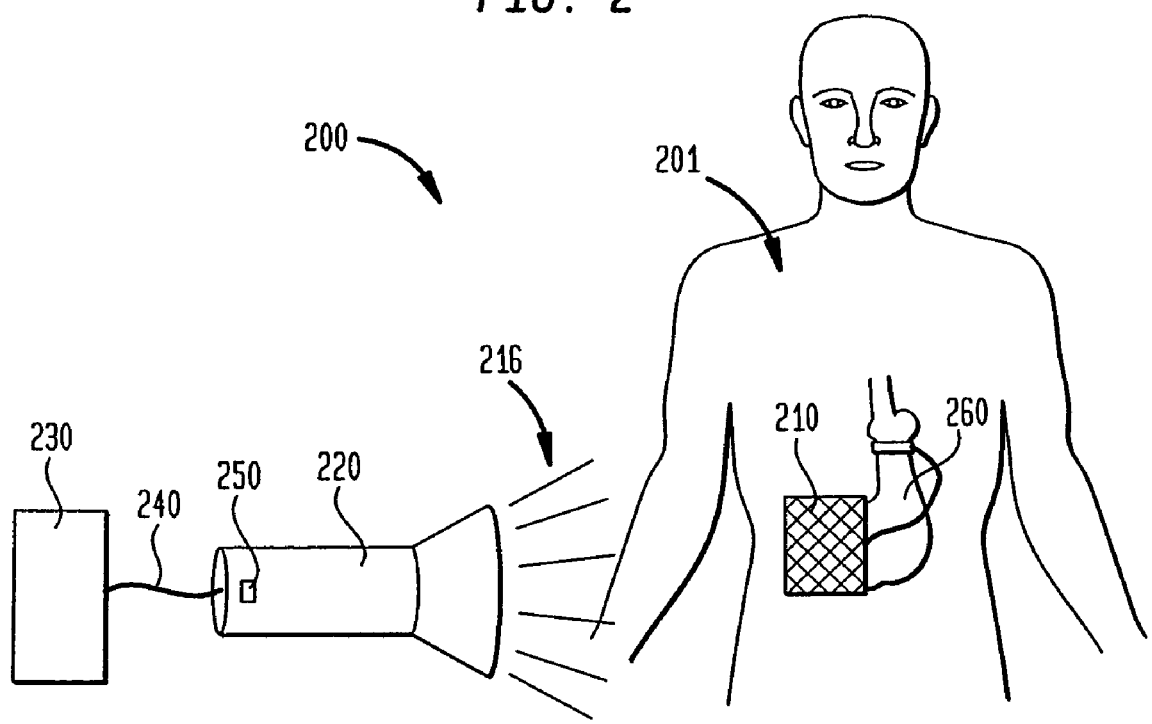
FIG. 2 is a representation of a light powering device for powering the food intake restriction system of FIG. 1.

In one exemplary embodiment shown in FIG. 2, the communicating member is in the form of a photovoltaic cell array or solar cell 210 adapted to receive light waves 216 from an external apparatus 200. The external energy apparatus 200 can include a light source that generates the light waves 216. The light source can be configured in many ways known in the art, but in the illustrated embodiment, it is in the form of a hand-held external device 220 that is electrically connected to a power source 230, such as an electrical outlet or a battery, via an electric cable 240. The external device 220 can also include a switch 250 that enables a user to turn the external device 220 on or off as needed. When the external device 220 is in the "on" position, it can be configured to generate light waves 216 in the infrared range of about 0.70 µm to 1,000 µm. Alternatively or in addition, the external device 220 can be configured to generate light waves 216 in the visible range of about 400 nm to 750 nm or light waves 216 in the ultraviolet range of about 250 nm to 400 nm. Although not shown in FIG. 2, the external device 220 can also include a gauge effective to indicate whether light waves 216 are being communicated between the external device 220 and the solar cell 210 that are effective to power and/or charge the implantable restriction device. The indication given by the gauge can take the form of any notification means known in the art, including a light, such as an LED, an audible noise, and/or a vibration. Alternatively, a silicon nanowire can convert light energy into electric energy on the scale to power low power sensor devices.

In an exemplary embodiment, in use the solar cell 210 can be implanted beneath a tissue surface, e.g., in a patient's abdomen or fascia layer. A user can position the external device 220 in proximity to the implanted solar cell 210 and direct the light waves 216 towards a surface of the solar cell 210 implanted near a surface of a patient's skin. The solar cell 210 can receive and absorb the light waves 216, convert the light waves 216 into electrical power using methods well known in the art, and store them in a device, for example, a capacitor or battery, for later use by the implantable restriction device. Alternatively, the solar cell 210 can immediately transfer the energy via a cable 260 and/or via a wireless transfer to power other devices within the implantable restriction device for monitoring and/or adjusting the gastric band or performing other tasks as described above.

Figure 3:
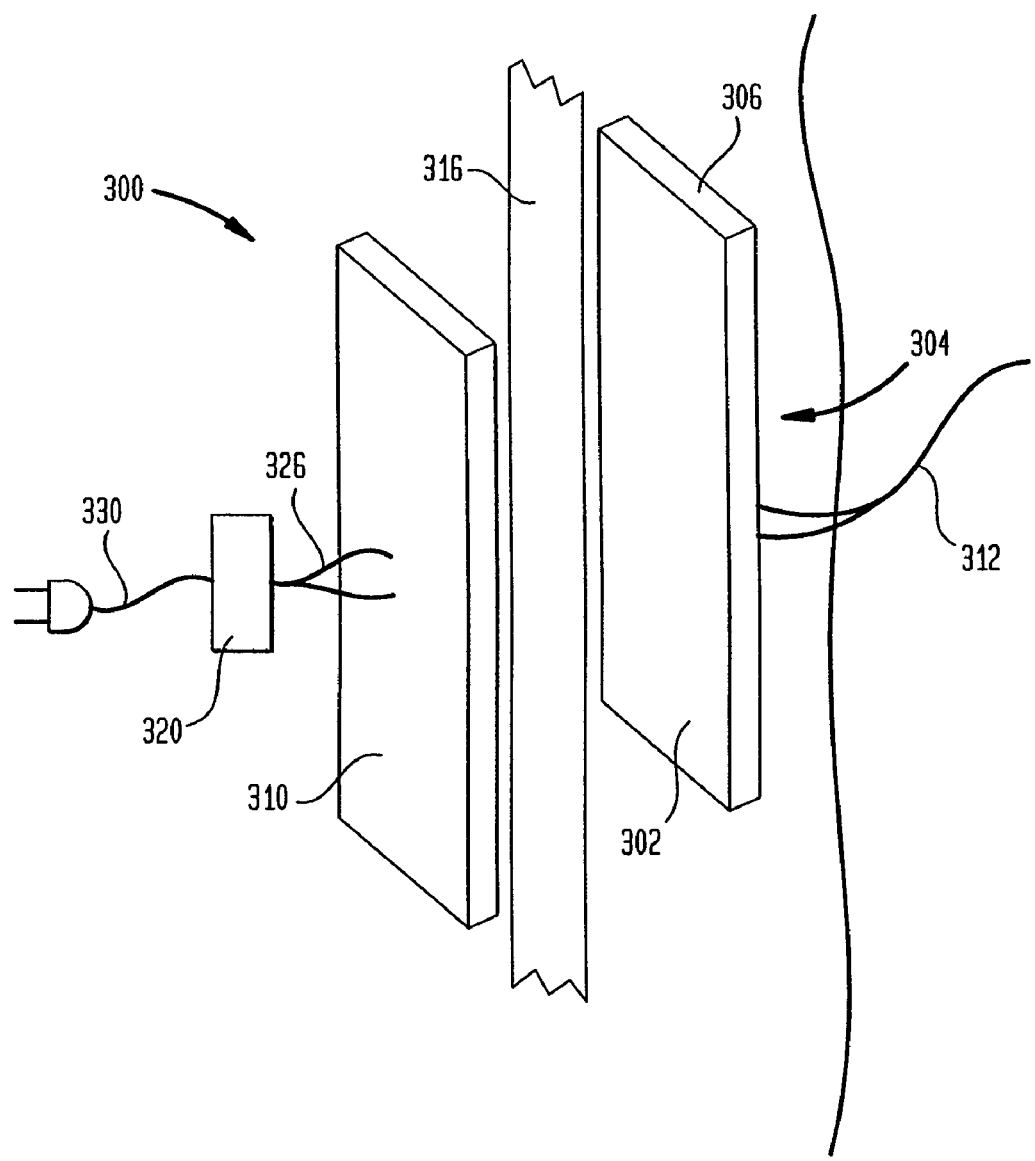
FIG. 3 is representation of a thermoelectric powering device for powering the food intake restriction system of FIG. 1.

In another embodiment shown in FIG. 3, the communicating member can be in the form of a thermoelectric generator 306, such as a Peltier device, configured to use a temperature differential to generate electricity. The external device can include a thermoelectric powering device 300 adapted to power an implantable restriction device implanted within a patient. In an exemplary embodiment, the generator 306 can be implanted under a patient's skin and a temperature differential can be created across the generator 306 by providing an external temperature source which is different than body temperature. As shown, the generator 306 includes a first side 302, which faces outward from the patient's body and is positioned just under the skin. The generator 306 also includes a second side 304 which faces towards an interior of the patient's body. The generator 306 includes electrical leads 312 which can be connected to a storage device, such as a capacitor or battery, or directly to the devices within the implantable restriction device. A means for monitoring the charge level of the storage device may also be included.

As shown in FIG. 3, the thermoelectric powering device includes a temperature source 310. A person skilled in the art will appreciate that the temperature source 310 can be any device or element which is capable of producing a temperature that is different than the temperature associated with the second side 304 of the generator 306. For example, if the temperature of the second side 304 of the generator 306 is at an anatomical reference temperature such as a human body temperature, then the temperature source 310 can be a piece of ice which is at a temperature cooler than the anatomical reference temperature. Alternatively, the first side 302 of the generator 306 can be placed in contact with a large blood vessel within the body, since the body uses the blood stream to convey heat to and from the body. A natural temperature gradient exists in the body between the blood vessel and the body, and therefore between the first side 302 and the second side 304, which can be used to generate power.

In an exemplary embodiment, in use, when a patient or physician places the temperature source 310, e.g. ice, against a tissue surface 316, in proximity to the first side 302 of the implanted generator 306, a temperature differential is created across the generator 306, thereby causing it to generate electricity. A patient and/or physician can place the temperature source 310 against an area of the patient's skin that covers the first side 302 of the implanted generator 306. The temperature source 310 will change the temperature of the first side 302 of the generator so that there is a difference in temperature between the first side 302 and the second side 304 effective to generate electricity. In another example, the temperature source 310 can be a second Peltier device used as a thermoelectric cooler so that one side of the device is much cooler than the temperature of the second side 304 of the implanted generator 306. The thermoelectric cooler can then be placed adjacent to the tissue surface 316 in proximity to the first side 302 of the implanted generator 306, thereby creating a temperature differential across the generator 306 to produce electricity. Alternatively, the temperature source 310 can be eddy-current heating of a conductive component connected to or within the implantable restrictive device. The eddy current may be generated by an inductive coupled external alternating power source. Heating may be controlled for example by the mass of the conductive component, the size and shape of the component, magnetic permeability of the conductive component, resistivity of the conductive component, external power coupling frequency or the external power output level, etc. In one exemplary embodiment, the heat source could be a heating pad placed on or near the tissue surface. The electricity which is generated can then be used by devices within the implantable restriction device as needed.

The temperature source 310 can alternatively be connected to or disposed within an external device 320. The external device 320 can include a gauge that indicates whether a temperature differential exists between the temperature source 310 and the generator 306 that is effective to charge and/or power the implantable restriction device. The indication given by the gauge can take the form of any notification means known in the art, including a light, such as an LED, an audible noise, and/or a vibration. If the temperature source 310 is ice or another temperature element which doesn't require electrical power, an external device 320 may not be required for the purpose of providing power. If the temperature source 310 is a thermoelectric cooler or other electrically powered temperature source as illustrated in FIG. 3, then the external device 320 can provide power to the temperature source 310 via electrical leads 326. The external source 320 can contain batteries or other power source, or can be connected to a wall power source via cable 330.

Figure 4:
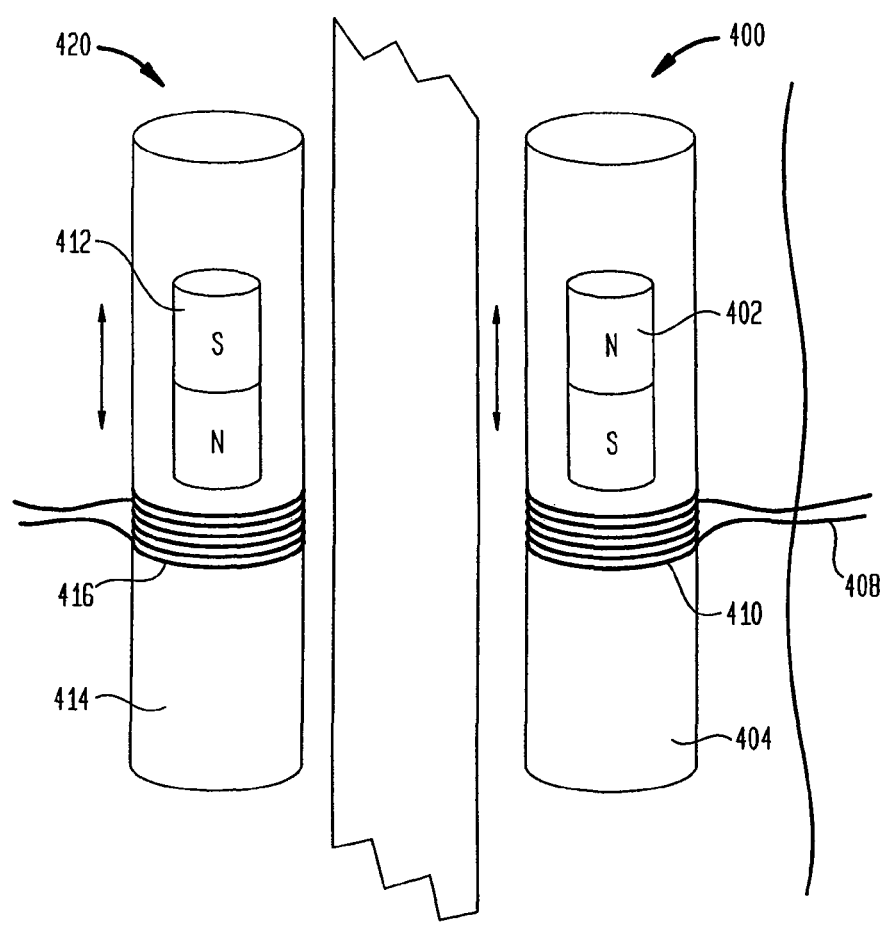
FIG. 4 is a representation of one embodiment of a kinetic motion powering device for powering the food intake restriction system of FIG. 1.

FIG. 4 shows another embodiment of a communicating member in the form of a kinetic motion apparatus 400 adapted to provide power to the implantable restriction device. In one exemplary embodiment, as shown, the kinetic motion apparatus 400 includes a housing having a magnet 402 disposed therein. The housing can be of any shape and made of any material known in the art, but in the illustrated embodiment, the housing is in the form of a glass tube or cylinder 404 having a metal or copper wire 410 wrapped tightly in a coil around an exterior surface of the cylinder 404. In this configuration, the kinetic motion apparatus 400 can generate electricity in the copper wire 406 by movement of the magnet 402 contained within the cylinder 404. Movement of the magnet 402 within the cylinder 404 will effectively cause the copper wire 410 to be moved through a magnetic field, thereby causing electricity to be generated, as will be appreciated by those skilled in the art. Electrical leads 408 coupled to the copper wire 410 are provided to carry the electricity generated by the kinetic motion apparatus 406 to a storage device or directly to devices within the implantable restriction device as needed. A means for monitoring the charge level of the storage device may also be included.

While many configurations are possible, in one exemplary embodiment, the kinetic motion apparatus 400 can be implanted within a patient's body such that physical movement of the body is effective to move the magnet 402 within the cylinder 404. For example, a patient can perform any movement, such as walking, running, jumping, shaking, etc., and this will cause the magnet 402 to move laterally, rotationally, or any combination thereof, within the cylinder 404 to generate electricity within the copper wire 406. In another example, the kinetic motion apparatus 400 may be implanted within a patient's body such that more subtle, but predictable physical movements within the body are effective in moving the magnet 402 within the cylinder 404. Examples of internal movements within the patient that may be harnessed include, but are not limited to, motions related to respiration (e.g., motions of the diaphragm), digestion (e.g., peristaltic waves through any portion of the gastrointestinal tract), and/or oscillatory motions within the circulatory system (e.g., pulsatile flow in the arterial system, motion of the heart, etc.).

Alternatively, or in addition, the kinetic motion apparatus 400 can include an external driver. In the embodiment shown in FIG. 4, the external driver is composed of the same elements as the kinetic motion apparatus 400, namely, a housing 414, a magnet 412, and a copper wire 416 to form an external electromagnet 420. The external electromagnet 420 can be manually driven by supplying the copper wire 416 with electricity to cause the magnet 412 to oscillate. As the magnet 412 oscillates, sympathetic oscillations are induced in the magnet 402 disposed within the kinetic motion apparatus 400, thereby causing electricity to be generated to supply power to the implantable restriction device. A person skilled in the art will appreciate that any driver or vibration element, internal or external, which is effective to produce oscillations, vibrations, or other motions in the magnet 402 within the kinetic motion apparatus 400, can be used to generate power. One additional alternative may include the conversion of oscillatory gradients in pressure created by natural and regularly occurring events such as respiration into fluid flows that induce oscillatory translational and/or rotational motions of the magnet 402. Moreover, the kinetic motion apparatus 400 can have a variety of other configurations in which energy is generated from motion or pressure gradients caused by these motions.

Although not shown in FIG. 4, an external device can also be provided to be in communication with the external driver and it can provide power to the external driver taken from a battery or other power source. The external driver can also include a gauge that indicates a charge status of the communicating member and/or whether there is proper alignment between an external driver and the kinetic motion apparatus 400. For example, the gauge can indicate whether circuitry and/or devices within the implantable restriction device need to be charged by the kinetic motion apparatus 400, or whether they are fully charged. Alternatively or in addition, the gauge can indicate proper alignment of an external driver that is attempting to generate sympathetic oscillations within the kinetic motion apparatus 400. The indication given by the gauge can take the form of any notification means known in the art, including a light, such as an LED, an audible noise, and/or a vibration.

Figure 5:
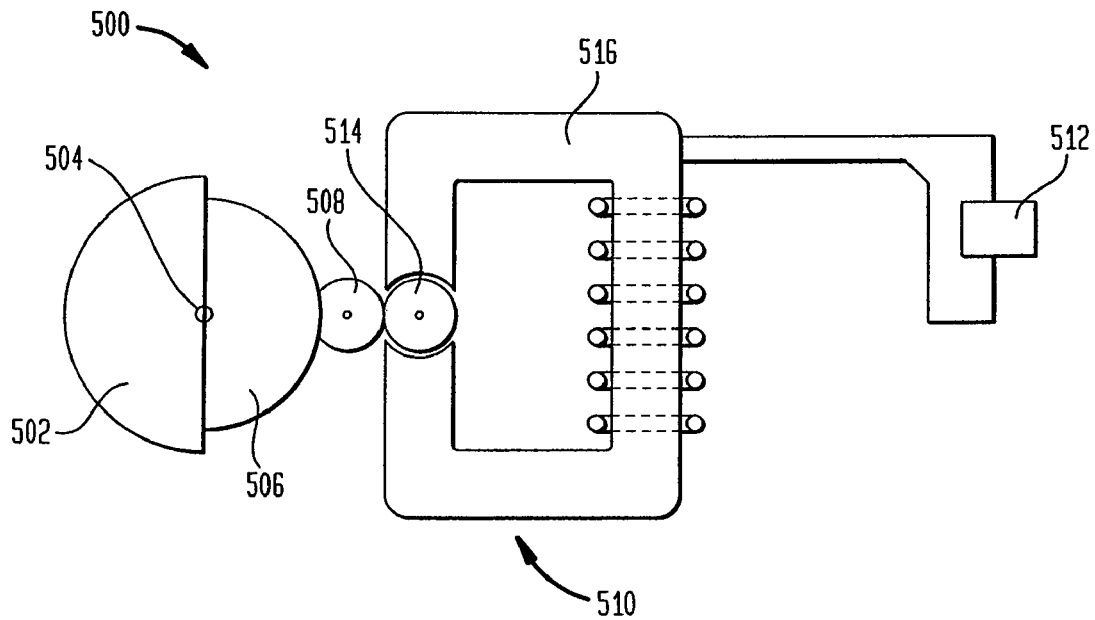
FIG. 5 is a representation of another embodiment of a kinetic motion powering device for powering the food intake restriction system of FIG. 1.

In another exemplary embodiment, a kinetic motion apparatus is provided that is operable to convert motion into energy to power the implantable restriction device. In one embodiment shown in FIG. 5, a kinetic motion apparatus 500 is provided and can include a counterweight 502 coupled to a shaft 504 such that the counterweight 502 can freely pivot about the shaft 504 in response to motion and movement of the patient. The counterweight 502 and the shaft 504 can be formed from any biocompatible material known in the art, including stainless steel, titanium, cobalt chrome, and any number of polymer plastics. A drive gear 506 can be nested within a hollow portion of the counterweight 502, and in one embodiment, it can be directly coupled to the counterweight 502 such the drive gear 506 moves in response to movement of the counterweight 502. The drive gear 506 can also be coupled to a drive train of an electric generator 510. As the drive gear 506 moves in response to the counterweight 502, it rotates a pinion gear 508 which in turn rotates the rotor 514 to a high velocity. This rotation then induces electric current through the stator 516 thereby charging the capacitor 512. The electric generator 510 thus converts mechanical energy from movement of the counterweight 503 into electrical energy.

The electrical energy produced by the generator 510 can be used to directly power the implantable restriction device or it can be stored within an accumulation element 512 for later use. In an exemplary embodiment, the accumulation element 512 can be a capacitor that contains lithium ion which provides an efficient conducting surface that may store energy longer than those capacitors typically made from other substrates. In another embodiment, the accumulation element 512 can be a high density ultracapacitor. A person skilled in the art will appreciate that any combination of gearing can be used to couple a patient's movement to the generator and any type of accumulation element 512 can be used to store charge.

Figure 6:
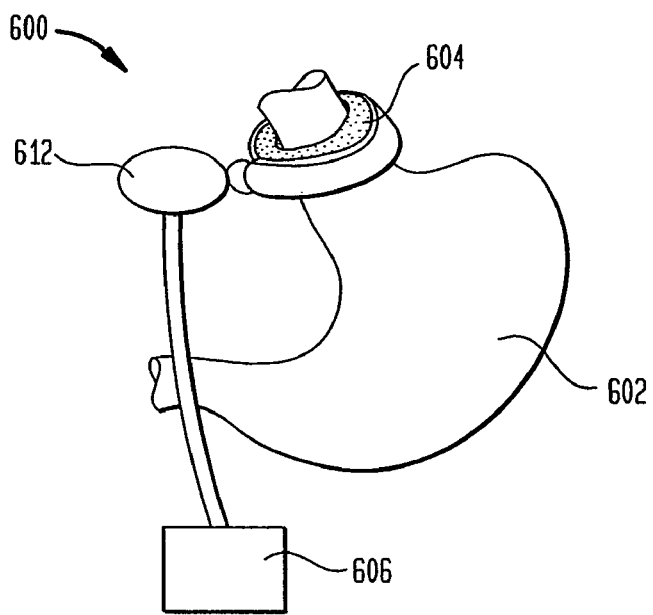
FIG. 6 is a representation of still another embodiment of a kinetic motion powering device for powering the food intake restriction system of FIG. 1.

In another embodiment shown in FIG. 6, a kinetic motion apparatus 600 is provided such that motion of a stomach 602 pushing against fluid in the gastric band 604 is converted into energy to supply power to a rechargeable battery or an accumulation element 606 that stores charge. As food passes through the band 604, pressure will increase and decrease in the gastric band 604. This vibration energy can be harvested by a variety of different methods known in the art such as electromagnetic, electrostatic, or piezoelectric conversion. In piezoelectric (piezo) methods, a bimorph based on piezoelectric materials vibrates, creating a charge that generates a voltage with amplitude proportional to the size and shape of the piezoelectric material, periodicity, and amount of force. Thus, the kinetic motion apparatus 600 can include a piezoelectric transducer element 612 attached to the gastric band 604 that can produce power proportional to the displacement and periodicity of band movement. This energy can then be stored in the accumulation element 606 until needed by the implantable restriction device. A person skilled in the art will appreciate that similar use can be made of electro-active polymer elements attached to the gastric band.

The internal devices disclosed herein are designed to be single use devices. The external devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application. The implantable devices disclosed herein are designed for single patient use.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for providing power to an implantable restriction device, comprising:

driving a communicating member implanted in a patient and coupled to an implantable restriction device implanted in a patient to power the implantable restriction device, wherein the communicating member includes a kinetic motion apparatus having a metal wire and a magnet, the magnet being configured to move relative to the metal wire to generate electrical energy that powers the implantable restriction device;

wherein the implantable restriction device comprises a gastric band disposed around a stomach to form a restriction, and a housing in communication with the gastric band;

wherein the kinetic motion apparatus is driven by an external oscillating electromagnet that induces sympathetic oscillations in the magnet.

2. The method of claim 1, wherein the magnet moves relative to the metal wire in response to motion by the patient.

3. The method of claim 1, wherein the kinetic motion apparatus is driven by a vibration element that causes the metal wire to move through the magnetic field.

4. The method of claim 1, wherein the kinetic motion apparatus includes a piezoelectric device that converts internal muscle and/or organ movement within a patient into energy to power the implantable restriction device.

5. The method of claim 1, wherein the kinetic motion apparatus includes a piezoelectric device that converts digestive motion of the stomach against the gastric band into electrical energy to power the implantable restriction device.

6. The method of claim 1, wherein the communicating member is in communication with an external device and the external device receives data from the communicating member, the data including at least one measurement of pressure of fluid within the implantable restriction device.

7. The method of claim 6, wherein the external device includes a gauge that indicates a charge status of the implantable restriction device.

8. The method of claim 1, wherein the communicating member determines a pressure of fluid within the implantable restriction device.

9. The method of claim 1, wherein excess energy from the kinetic motion apparatus is stored for later use in a storage device for storing electrical energy.

10. A method for powering an implantable gastric band, comprising:
    aligning an external driver that is positioned external to the patient with a kinetic motion apparatus that is implanted in a patient;
    delivering electrical current to the external driver, causing a magnet disposed in the external driver to oscillate and thereby inducing sympathetic oscillations in a magnet disposed in the kinetic motion apparatus;
    wherein oscillation of the magnet disposed in the kinetic motion apparatus generates electrical current that provides power to a gastric band that is implanted in the patient.

11. The method of claim 10, wherein the external driver includes a gauge that indicates proper alignment between the external driver and the kinetic motion apparatus.

12. The method of claim 10, wherein excess energy from the kinetic motion apparatus is stored for later use in a storage device for storing electrical energy.

* * * * *